(12) United States Patent
Soo et al.

(10) Patent No.: US 10,219,876 B2
(45) Date of Patent: Mar. 5, 2019

(54) METHOD OF MAKING A CUSTOMIZED ORTHODONTIC BRACKET

(71) Applicant: 3M INNOVATIVE PROPERTIES COMPANY, St. Paul, MN (US)

(72) Inventors: Philip P. Soo, Woodbury, MN (US); James D. Cleary, Glendora, CA (US); Arno Hohmann, Munich (DE); Ralf Paehl, Melle (DE)

(73) Assignee: 3M Innovative Properties Company, St. Paul, MN (US)

( * ) Notice: Subject to any disclaimer, the term of this patent is extended or adjusted under 35 U.S.C. 154(b) by 111 days.

(21) Appl. No.: 15/118,742

(22) PCT Filed: Feb. 10, 2015

(86) PCT No.: PCT/US2015/015129
§ 371 (c)(1),
(2) Date: Aug. 12, 2016

(87) PCT Pub. No.: WO2015/123170
PCT Pub. Date: Aug. 20, 2015

(65) Prior Publication Data
US 2017/0049534 A1  Feb. 23, 2017

(30) Foreign Application Priority Data
Feb. 12, 2014 (EP) .................................. 14154796

(51) Int. Cl.
*A61C 7/14* (2006.01)
*A61C 7/00* (2006.01)
(Continued)

(52) U.S. Cl.
CPC .............. *A61C 7/002* (2013.01); *A61C 7/16* (2013.01); *A61C 13/0004* (2013.01);
(Continued)

(58) Field of Classification Search
CPC ............ A61C 13/0004; A61C 13/0013; A61C 13/0018; A61C 13/0019; A61C 13/00;
(Continued)

(56) References Cited

U.S. PATENT DOCUMENTS 6,846,179 B2    1/2005  Chapouland et al.
8,813,364 B2 *  8/2014  Schechner ......... A61C 13/0004
                                                        29/896.11
(Continued)

FOREIGN PATENT DOCUMENTS

EP           2428179          3/2012
WO    WO 2006/083088          8/2006
(Continued)

OTHER PUBLICATIONS

International Search Report for PCT International Application No. PCT/US2015/015129, dated Apr. 22, 2015, 4 pages.

*Primary Examiner* — Jun S Yoo

(57) ABSTRACT

A method of making a customized orthodontic bracket includes steps of providing a pre-manufactured physical bracket body, providing a physical bracket base having a tooth facing side shaped according to of at least part of a patient's tooth, and joining the bracket body and at least a portion of the bracket base. The bracket base is provided using a material build-up process. The invention helps facilitating manufacturing of customized orthodontic brackets.

11 Claims, 3 Drawing Sheets

(51) Int. Cl.
*A61C 7/16* (2006.01)
*A61C 13/00* (2006.01)
*B22F 3/105* (2006.01)
*B22F 7/08* (2006.01)
*B33Y 80/00* (2015.01)
*B33Y 10/00* (2015.01)

(52) U.S. Cl.
CPC ...... *A61C 13/0018* (2013.01); *A61C 13/0019* (2013.01); *A61C 13/0022* (2013.01); *B22F 3/1055* (2013.01); *B22F 7/08* (2013.01); *B33Y 10/00* (2014.12); *B33Y 80/00* (2014.12); *Y02P 10/295* (2015.11)

(58) Field of Classification Search
CPC ........... A61C 5/77; A61C 7/002; A61C 7/145; A61C 7/141; A61C 7/14
See application file for complete search history.

(56) References Cited

U.S. PATENT DOCUMENTS

| | | | |
|---|---|---|---|
| 8,944,811 | B2 | 2/2015 | Curie et al. |
| 9,949,804 | B2* | 4/2018 | Schlimper .............. A61C 7/002 |
| 2004/0197737 | A1 | 10/2004 | Uckelmann et al. |
| 2012/0015315 | A1 | 1/2012 | Wiechmann et al. |
| 2013/0125398 | A1 | 5/2013 | Curie et al. |
| 2013/0266906 | A1 | 10/2013 | Soo |
| 2014/0234552 | A1* | 8/2014 | Frankenberger ....... B64D 43/00 427/555 |

FOREIGN PATENT DOCUMENTS

| | | |
|---|---|---|
| WO | WO 2012/107501 | 8/2012 |
| WO | WO 2012/107503 | 8/2012 |
| WO | WO 2012/107505 | 8/2012 |
| WO | WO 2012/116877 | 9/2012 |

* cited by examiner

METHOD OF MAKING A CUSTOMIZED ORTHODONTIC BRACKET

CROSS REFERENCE TO RELATED APPLICATIONS

This application is a national stage filing under 35 U.S.C. 371 of PCT/US2015/015129, filed Feb. 10, 2015, which claims the benefit of European Application No. 14154796.8, filed Feb. 12, 2014, the disclosure of which is incorporated by reference in its/their entirety herein.

FIELD OF THE INVENTION

The invention relates to a method of making a customized orthodontic bracket and in particular to a method in which a pre-manufactured physical bracket body is combined with a three-dimensionally built up bracket base. Further the invention relates to a bracket obtainable with the method of the invention.

BACKGROUND ART

Orthodontic brackets are generally used in orthodontic treatments for moving one or more teeth from an initial position to a desired position in a patient's dentition. The initial position typically refers to a position at the beginning of an orthodontic treatment, for example a position in which the labial faces of the teeth are misaligned to each other, whereas in the desired position the labial faces of the same teeth may be generally aligned. For example the patient's teeth may be aligned relative to each other to provide the dentition with a more aesthetically pleasant appearance. Further one or more teeth may be moved within the dentition to compensate for a malocclusion. Such a movement of a tooth or teeth can be typically achieved by using one or more brackets attached to one or more teeth. The brackets are typically connected to an elastic archwire for applying forces to the teeth urging them toward desired positions over a longer term.

Often orthodontic brackets are off-the-shelf products which are configured for use with clinical situations of different patients. Further there are customized orthodontic brackets which are typically made to fit with an individual clinical situation of one particular patient.

For example US 2012/0015315 A1 discloses a customized orthodontic bracket system which includes a bracket having a customized bracket bonding pad for bonding the bracket to a tooth of a patient and a bracket slot adapted to receive a customized archwire. The customized archwire is adapted to be positioned in the bracket slot to form a precise bracket slot-archwire interface.

Although a variety of different brackets and bracket systems are on the market there is still a desire to provide brackets which on the one hand match an individual clinical situation and on the other hand are minimized in costs for manufacturing and costs for application to a patient's teeth. Typically the minimization of costs in the manufacturing must be balanced relative to the desired accuracy of the customized brackets. For example
brackets should be placeable easily and precisely to a patients teeth, and should have a geometry allowing an orthodontic archwire to be attached or slidably coupled precisely at desired positions relative to the teeth. Further customized brackets should be sufficiently durable over the time period of an orthodontic treatment. On the other hand available manufacturing methods for mass production of customized brackets may not be compatible with such precision and quality requirements, whereas available sufficiently precise and high quality manufacturing methods may not satisfy or fully satisfy requirements for mass production at commercially viable costs.

SUMMARY OF THE INVENTION

The invention relates in one aspect to a method of making a customized orthodontic bracket. A customized orthodontic bracket typically has a bracket base for attaching the bracket to a patient's tooth and a bracket body for retaining an archwire. The bracket base typically has a tooth facing side for bonding the bracket to the tooth. In contrast to so-called off-the-shelf orthodontic brackets which typically have standardized bracket bases, the bracket base of a customized orthodontic bracket typically is individually shaped in accordance to a shape of the tooth to which the bracket is intended to be bonded. In particular the tooth facing side of the bracket base of the customized orthodontic bracket is typically overall shaped to conform to a portion or area of the outer tooth surface. Typically the tooth facing side of the customized orthodontic bracket has a footprint (or outer periphery) and the portion of the outer tooth surface corresponds in size and shape to that footprint. The term "conform" in this context means that the overall shape of the tooth facing side and the overall shape of the tooth portion correspond to each other, although a surface structure of the tooth facing side may be different from the surface structure of the tooth. For example the tooth facing side may comprise a roughened surface or a surface having a plurality of retention features (for example a mesh-type surface or mushroom pins), but may still overall conform to the shape of the tooth portion.

The method comprises the steps of:
providing a pre-manufactured physical bracket body for retaining an orthodontic archwire;
providing a virtual bonding surface in the form of a three-dimensional shape of at least part of a patient's tooth;
providing a physical bracket base using a material build-up process, the bracket base having a tooth facing side that is shaped based on the virtual bonding surface; and
joining the bracket body and at least a portion of the bracket base.

This invention is advantageous in that it allows a serial production of a part of a multiplicity of brackets while another part of these brackets can be customized to individual teeth of patients. Further this invention allows manufacturing of an archwire slot within the bracket body at a maximized accuracy to provide a precise and durable fit between the bracket body and the archwire, whereas the accuracy of the overall bracket shape can be adapted to the needs of an individual clinical situation of a patient. Further different materials can be used for the bracket base and the bracket body, for example to provide a relatively hard bracket body for durably holding the archwire and to provide a softer bracket base to prevent the bracket to break upon exposure of mechanical forces (for example during chewing action). This invention is further advantageous in that it helps minimizing costs in the manufacturing. Further, this invention does not require, but may still utilize, the use of expensive materials like gold.

Preferably, in certain circumstances, the pre-manufactured physical bracket body has an archwire slot for receiving an archwire. Typically an archwire as used with brackets obtainable by the method of the invention extends at a rectangular cross-section and the archwire slot is shaped and sized to fit with at least two opposing sides of that cross-section. Thus the connection between the archwire and the bracket body allows a torque to be transmitted between the archwire and the bracket.

In one embodiment, the step of providing a physical bracket base is performed in a three-dimensional material build-up device, sometime also referred to as "3D printer". The step of providing the pre-manufactured physical bracket body may further comprise positioning the bracket body from a place outside the material build-up device into the material build-up device. For example the bracket body may be pre-manufactured by processes other than a material build-up process, for example by casting and/or machining.

In a further embodiment the method comprises the steps of:
  building up the bracket base as individual pre-manufactured piece; and
  joining the bracket body and the bracket base.

In this embodiment, both the bracket base and the bracket body are initially pre-manufactured and subsequently joined, for example by assembly. The pre-manufactured bracket body preferably has a bracket base interface in the form of a surface for connection of the bracket body with the bracket base. Further, the pre-manufactured bracket base preferably has a bracket body interface in the form of a surface for connection of the bracket base with the bracket body. The bracket base and the bracket body may be joined by welding, gluing or by a positive fit (for example a screw connection or interference fit). The bracket base interface and the bracket body interface may be shaped for mating with one another in one definite position, for example one may have the negative shape of the other.

In a further embodiment the method comprises the step of building up the bracket base on the bracket body. The pre-manufactured bracket body also can preferably have a bracket base interface in the form of a surface for connection of the bracket body with the bracket base. The bracket base interface is typically arranged opposite of the archwire slot. Further, a bracket base interface is preferably, in certain circumstances, used in this embodiment for building up the bracket base thereon by a material build-up process.

The method may further comprise the step of providing a primer layer on the bracket body, in particular on the bracket base interface of the bracket body, and building up the bracket base on the primer layer. The primer layer may comprise a metal alloy and a flux melting agent. Thus, using for example Selective Laser Melting (SLM), a stable connection between the bracket base and the bracket body may be achieved.

In a further embodiment the method further comprises the steps of providing a plurality of differently shaped pre-manufactured physical bracket bodies. Further, the step of providing the pre-manufactured physical bracket body may comprise selecting a particular pre-manufactured physical bracket body out of the plurality of differently shaped pre-manufactured physical bracket bodies. The method may further comprise the step of providing a physical library holding several bracket bodies of the same shape. For example the library may hold several types of bracket bodies and further several bracket bodies of the same type. The differently shaped pre-manufactured physical bracket bodies may comprise bracket bodies each extending along a given longitudinal axis and in which the archwire slots are inclined at different angles relative to the respective longitudinal axis. Thereby brackets having any of a variety of possible pre-scriptive values of torque, tip, and angulation in three-dimensional space may be provided. The library may offer different types of brackets in an assorted manner, for example one type of brackets in which the archwire slot extends along an axis which is inclined by about 5 degrees relative to the longitudinal axis and further types in which the archwire slot extends along an axis which is inclined by about 10, 15, 20, 25, 30, 35, 40, 45, 50, 55, 60, 65, 70, 75, 80, 85 or 90 degrees and so forth. The library may further hold a type of brackets in which the archwire slot extends along the longitudinal axis. The skilled person will recognize that other angles, for example intermediate or additional angles, are possible as needed.

In a preferred embodiment the material build-up process is based on Selective Laser Melting (SLM), in particular Direct Metal Laser Sintering (DMLS). The material for the material build-up process may be stainless steel, cobalt-chrome alloy, a gold alloy, a silver alloy and a titanium alloy. Therefore at least one or both of the bracket body and the bracket base may be made of one of a cobalt-chrome alloy, a gold alloy, a silver alloy and a titanium alloy. Other materials like any suitable stainless steel may be used.

The method may further comprise steps for determining the shape of the bracket and in particular for determining the shape of the bracket base. The shape of the bracket and/or the shape of the bracket base may be provided in a computer processible format and used in the material build-up process to make the bracket/bracket base.

The method may particularly comprise the steps of:
  providing a virtual model of a patient's teeth;
  identifying an area on at least one of the teeth and based thereon providing the virtual bonding surface; and
  determining an archwire position relative to the identified area or virtual bonding surface.

Preferably the virtual model of the patient's teeth is obtained from scanning the actual teeth of the patient intra-orally, or from scanning a physical model (for example a plaster model cast from a dental impression) of the patient's teeth. It is further possible to scan a dental impression taken from the patient's teeth. Typically an area is identified on several of the patient's teeth within the virtual model. The identified area or a copy thereof is preferably provided as the virtual bonding surface. The skilled person will recognize that this can be done by computer operation, for example by Computer Aided Design (CAD) software allowing creation and manipulation of three-dimensional computer models. Further, the skilled person will recognize that the mentioned areas can be identified physically on the patient's teeth or the model of the patient's teeth and captured to provide the virtual bonding surface.

The archwire position relative to the identified area or virtual bonding surface may be determined with aid of one or more computers. For example a three-dimensional virtual model of the archwire (for example in the form of a simple line) may be placed in relation to the virtual model of the patient's teeth by a user, for example by an orthodontist or a dental technician. Typically the so-called straight wire approach is used, meaning that a U-shaped archwire model extending in a plane may be provided by the computer, and the user may electronically deform that archwire model toward the patient's dentition model, with or without deforming the archwire outside that plane. Once the path along which the archwire runs is defined the bracket can be designed or configured as a connector between the archwire and the virtual bonding surface. The method therefore may comprise the step of providing the physical tooth facing side of the bracket base in a geometric relationship corresponding to the position of the identified area or virtual bonding surface relative to the archwire position of the bracket body. The design may be performed on a CAD system which is connectable to a library holding a plurality of standardized virtual bracket bodies. Such virtual bracket bodies preferably represent the physical bracket bodies used in the method of the invention. Further the CAD system preferably allows the bracket base to be designed based on the virtual bonding surface. For example the virtual bonding surface (or a copy thereof) may be used to form the shape of the tooth facing side of the bracket bonding pad and an offset of the virtual bonding surface may be used as a rear side or outward-facing side (opposite of the tooth facing side) of the bracket bonding pad. The bracket body may be selected and positioned such that it connects the archwire and the bonding pad to each other. A so formed computer design may be exported in the form of computer processible data to a material build-up device, for example an SLM device, in which the bracket is completed as described above.

In one embodiment, the method comprises the step of shortening the physical bracket body based on the archwire position and the identified area or virtual bonding surface. For example the library holding the physical bracket bodies may comprise precursors of the bracket bodies which form overlong versions of the bracket bodies, and the precursors may be cut to obtain the bracket body. Thus, the number of unique bracket bodies kept in the library may be minimized.

In a further aspect, the disclosure relates to a customized orthodontic bracket obtainable from the methods described above.

The skilled person will recognize that an orthodontic bracket may encompass, for example, bondable tubes, splints, buttons, cleats and other appliance as appropriate.

DETAILED DESCRIPTION OF THE INVENTION

Figure 1:
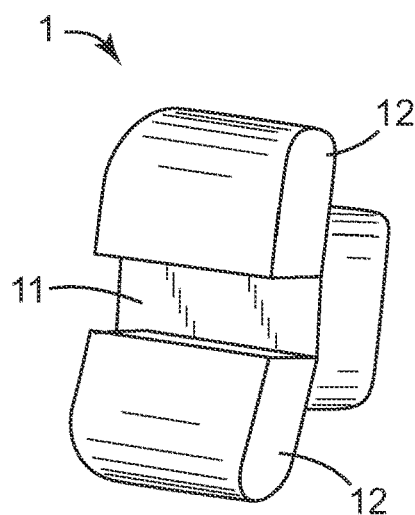
FIG. 1 is a perspective fragmentary view of a bracket body according to an embodiment of the invention.

FIG. 1 shows a physical bracket body 1. The bracket body 1 has an archwire slot 11 and, in the example, two wings 12, although in other examples the bracket body may have only one wing or three, four or more wings. The bracket body may further comprise one or more hooks (not shown). The wings 12 are configured for retaining an elastic tie (or rubber ring—not shown) and securing an archwire (also not shown) within the slot 11. The bracket body 1 in the example is pre-manufactured, for example cast, machined, or a combination thereof. Preferably the bracket body 1 is made of metal, for example, a cobalt-chrome alloy or a gold alloy.

Figure 2A:
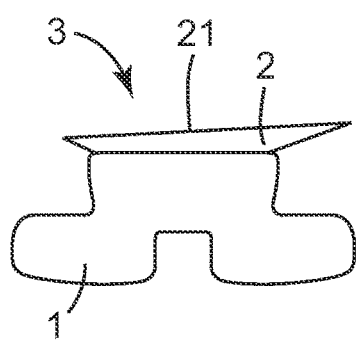
FIGS. 2A-2C is a side view of a set of brackets according to an embodiment of the invention.
Figure 2B:
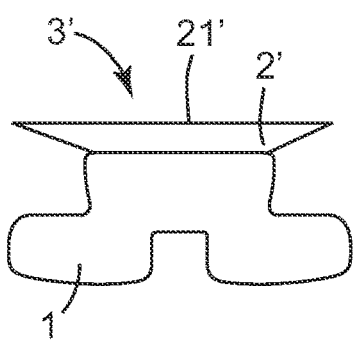
Figure 2C:
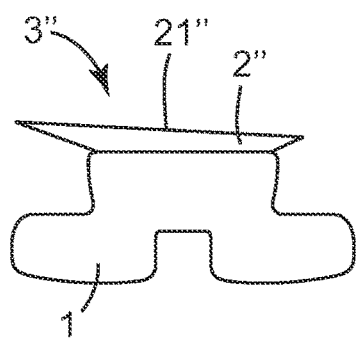

FIGS. 2A, 2B and 2C show three customized orthodontic brackets 3, 3', 3" made up from generally identical bracket bodies 1 and three customized and therefore differently shaped bracket bases 2, 2' and 2". Each of the bracket bases 2, 2' and 2" has a tooth facing side 21, 21', 21" that is shaped to conform to an outer shape of a portion of a patient's tooth. The bracket body 1 and the bracket base 2/2'/2" are joined—as explained in more detail further below—to form a customized or patient specific orthodontic bracket 3/3'/3".

Figure 3A:
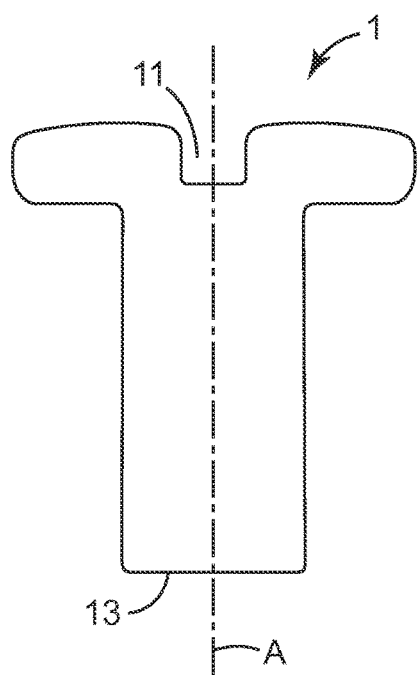
FIG. 3 is a schematic illustration of a library holding different bracket bodies according to an embodiment of the invention.
Figure 3B:
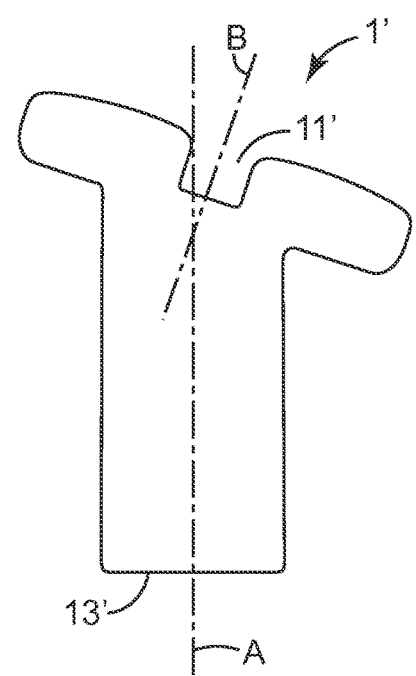

FIG. 3 illustrates a library of differently shaped physical bracket bodies 1, 1'. Such a library may have a multiplicity of differently shaped physical bracket bodies rather than only two as shown by way of example only. The library particularly holds bracket bodies 1, 1' which extend along a longitudinal axis A but which on the other hand have archwire slots that are inclined at different angles relative to the respective longitudinal axis A. For example, a first bracket body 1 has a first archwire slot 11 and a second bracket body 1' has a second archwire slot 11'. The first archwire slot 11 extends generally along the longitudinal axis A, whereas the second archwire slot 11' extends along a slot axis B being inclined with respect to the longitudinal axis A. For the purpose of the present specification the longitudinal axis may correspond to a center axis of a body in a dimension approximately between the archwire slot and the end of the body opposite thereof. Further, for the purpose of the present specification the slot axis may correspond to a middle axis of the slot in a dimension between the slot opening and the opposite slot dead end. The axes A and B may be oriented along any angle relative to each other (including in directions out of the plane of the page in FIG. 3).

The library may hold a plurality of bracket bodies each having a slot extending along a slot axis, wherein the individual slot axes are inclined with respect to the respective longitudinal axis A at different angels. For example, the library may hold a series of bracket bodies having slot axes at inclination angles graded by about 5 degrees, for example a bracket body having a slot axis inclined by 5 degrees, a further bracket body having a slot axis inclined by 10 degrees and so forth. Further, the bracket bodies 1, 1' of the library have a bracket base interface 13, 13'. The library may hold multiple bracket bodies having bracket base interfaces which are inclined at different angles, for example graded by angles of about 5 degrees.

An appropriate bracket body may be selected from the library as follows:

The shape of a patient's dentition (upper and/or lower jaw) with the teeth in the initial positions may be captured in the form of a three-dimensional computer model, either by scanning the patient's dentition intra-orally or by scanning a dental impression of the patient's dentition or a physical model of such dental impression. Such a computer model is further referred to as "virtual malocclusion model".

A set-up model of the patient's dentition may be provided physically or in the form of a computer model. The set-up model typically represents the patient's teeth in the target position after the orthodontic treatment. A physical set-up model may be captured or scanned to provide a computer set-up model, further referred to as "virtual set-up model". The virtual set-up model may be used to define a path along which an archwire runs and to determine the archwire position relative to one, more than one, or each of the teeth in the patient's dentition.

One or both of the virtual malocclusion model and the set-up model may be used to define a virtual bonding surface of the brackets. In particular an area may be identified on the labial or lingual surface of individual teeth in the model. Such area is a representation of a physical area on a tooth on which a tooth facing side of the bracket may be bonded. The area is typically selected to be large enough to cover a sufficient area so that an orthodontist can place the bracket on the corresponding tooth in one definite position. Typically the area further covers approximately 60-75 percent of the labial or lingual surface of a tooth to provide both good adhesion and to facilitate correct positioning.

Once the virtual bonding surface is determined the bracket base may be designed, for example using Computer Aided Design (CAD) software to provide a virtual model of the bracket base. Further the bracket body may be selected based on the geometric relationship between the virtual bonding surface and the archwire position. For example if the virtual bonding surface is inclined with respect to a rectangular archwire a bracket body with an appropriately inclined bracket slot may be selected. The skilled person will recognize that the design of the bracket base may be performed before or after selection of the bracket body. However the design of the bracket base is preferably also performed based on the geometric relationship between the virtual bonding surface and the archwire position.

The library may further comprise bracket bodies having an overlength. Such bracket bodies may be cut to a desired length to thereby form the bracket base interface at the shortened bracket body, thus removing at least a portion of the overlength. Cutting may be performed to further provide the bracket base interface at a desired angle.

Figure 4:
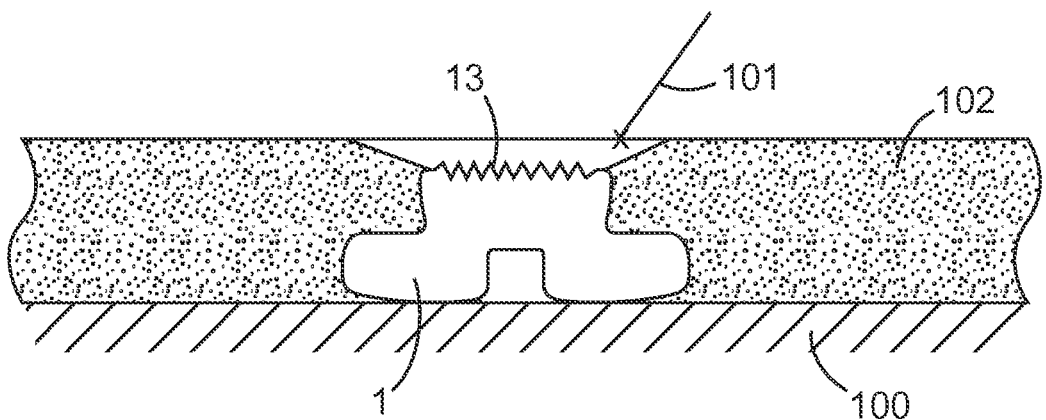
FIG. 4 is a cross-sectional view illustrating the method according to an embodiment of the invention.

FIG. 4 shows a bracket body 1 placed in a three-dimensional material build-up device 100 (not shown in detail). Such a three-dimensional material build-up device is also often referred to as "3D printer" in the technical field and in the example is a Selective Laser Melting (SLM) device. The bracket body 1 is placed at a determined reference position. Such a reference position preferably comprises information about a position of the bracket body 1 in a coordinate system of the device as well as an orientation of the bracket body 1 in that coordinate system. In the example the bracket body 1 is embedded in a metal powder 102 with the bracket base interface 13 oriented toward the free surface of that powder 102. A thin layer of powder covers the bracket base interface 13 and a laser beam 101 is used to sinter the bracket base layerwise onto the bracket body 1. The positioning of the laser beam 101 is computer numerically controlled in accordance with the virtual model of the bracket base and in appropriate geometric relationship to the bracket body 1. As illustrated by the zig-zag line the bracket base interface 13 is roughened to maximize bond strength between the bracket base 2 and the bracket body. The skilled person will recognize alternative three-dimensional material build-up processes. For example a metal wire may be used to be melted off by the laser instead of using a powder bed.

Figure 5:
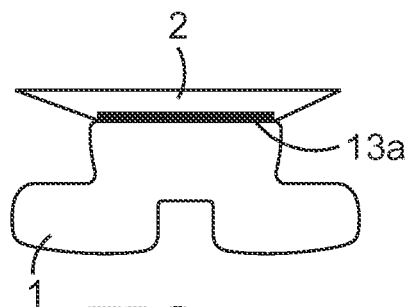
FIG. 5 is a partial view of a bracket according to an embodiment of the invention, made by the method illustrated in FIG. 4.

FIG. 5 shows a bracket body 1 and a bracket base 2 with a primer layer 13a arranged therebetween. Such primer layer 13a may maximize the quality of the sintering at the bracket base interface 13. The primer layer 13a may be made from an alloy having a high degree of compatibility and wetting with respect to both the bracket body 1 and the metal used in the SLM process.

Figure 6:
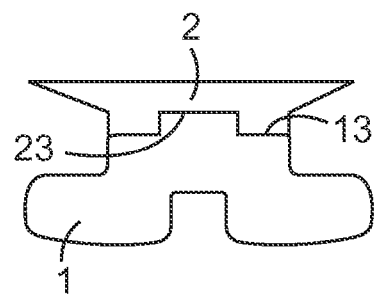
FIG. 6 is a side view of a bracket assembled from a pre-manufactured bracket base and a pre-manufactured bracket body according to an embodiment of the invention.

FIG. 6 shows a bracket body 1 and a bracket base 2 which are individually pre-manufactured and joined afterwards. The bracket base 2 may be manufactured using a three-dimensional build-up process. The bracket base 2 may have a bracket body interface 23 having the negative shape of the bracket base interface 13 of the bracket body 1. Thus the bracket base 2 and the bracket body 1 can be mated in a pre-determined and precise position with respect each other at the bracket body interface 23 and the bracket base interface 13, respectively.

The invention claimed is:

1. A method of making a customized orthodontic bracket, comprising the steps of:
    providing a pre-manufactured physical bracket body for retaining an orthodontic archwire;
    providing a primer layer on the bracket body;
    providing a virtual bonding surface in the form of a three-dimensional shape of at least part of a patient's tooth;
    providing a physical bracket base using a material build-up process to build up the bracket base on the primer layer of the bracket body, the bracket base having a tooth facing side that is shaped based on the virtual bonding surface; and
    joining the bracket body and at least a portion of the bracket base.

2. The method of claim 1, wherein the step of providing a physical bracket base is performed in a three-dimensional material build-up device, and wherein the step of providing the pre-manufactured physical bracket body comprises positioning the bracket body from a place outside the material build-up device into the material build-up device.

3. The method of claim 1, further comprising the step of providing a plurality of differently shaped pre-manufactured physical bracket bodies, wherein the step of providing the pre-manufactured physical bracket body comprises selecting a particular pre-manufactured physical bracket body out of the plurality of differently shaped pre-manufactured physical bracket bodies.

4. The method of claim 3, further comprising the step of providing a physical library holding several bracket bodies of the same shape.

5. The method of claim 3, wherein the differently shaped pre-manufactured physical bracket bodies comprise bracket bodies each having an archwire slot, the bracket bodies each extending along a longitudinal axis and in which the archwire slots are inclined at different angles relative to the respective longitudinal axes.

6. The method of claim 1, wherein the material build-up process is based on Direct Metal Laser Sintering (DMLS).

7. The method of claim 1, wherein at least one or both of the bracket body and the bracket base is made of one of a stainless steel, cobalt-chrome alloy, a gold alloy, a silver alloy and a titanium alloy.

8. The method of claim 1, further comprising the steps of:
    providing a virtual model of a patient's teeth;
    identifying an area on at least one of the teeth and based thereon providing the virtual bonding surface; and
    determining an archwire position relative to the identified area or virtual bonding surface.

9. The method of claim 8, further comprising the step of shortening the bracket body based on the archwire position and the identified area or virtual bonding surface.

10. The method of claim 8, further comprising the step of providing the physical tooth facing side of the bracket base in a geometric relationship corresponding to the position of the identified area or virtual bonding surface relative to the archwire position of the bracket body.

11. A customized orthodontic bracket, obtainable from the method of claim 1.

* * * * *